United States Patent
Staneker et al.

(10) Patent No.: US 10,751,106 B2
(45) Date of Patent: Aug. 25, 2020

(54) ELECTROSURGICAL INSTRUMENT AND DEVICE WITH SUCH AN INSTRUMENT

(71) Applicant: Erbe Elektromedizin GmbH, Tübingen (DE)

(72) Inventors: Peter Staneker, Engstingen (DE); Thorsten Rombach, Gomaringen (DE); Udo Kirstgen, Rottenburg (DE)

(73) Assignee: Erbe Elektromedizin GmbH, Tübingen (DE)

( * ) Notice: Subject to any disclaimer, the term of this patent is extended or adjusted under 35 U.S.C. 154(b) by 794 days.

(21) Appl. No.: 15/147,587

(22) Filed: May 5, 2016

(65) Prior Publication Data
US 2016/0331438 A1    Nov. 17, 2016

(30) Foreign Application Priority Data

May 11, 2015 (EP) ..................................... 15167061

(51) Int. Cl.
*A61B 18/14*    (2006.01)
*A61B 18/04*    (2006.01)
(Continued)

(52) U.S. Cl.
CPC ........ *A61B 18/042* (2013.01); *A61B 18/1492* (2013.01); *A61B 2017/00292* (2013.01);
(Continued)

(58) Field of Classification Search
CPC .............. A61B 18/042; A61B 18/1492; A61B 2017/00292; A61B 2017/00309;
(Continued)

(56) References Cited

U.S. PATENT DOCUMENTS 5,295,614 A * 3/1994 Chang .................... B05C 17/01
                                                                222/137
5,456,683 A    10/1995 Fritzsch et al.
(Continued)

FOREIGN PATENT DOCUMENTS

DE    1414810 C1    8/1995
EP    0634139 A1    1/1995
(Continued)

OTHER PUBLICATIONS

European Search Report from corresponding European Application No. 15 16 7061, dated Nov. 15, 2015, 7 pages. X.
(Continued)

*Primary Examiner* — Jaymi E Della
*Assistant Examiner* — Sean W Collins
(74) *Attorney, Agent, or Firm* — Fitch, Even, Tabin, & Flannery LLP

(57) ABSTRACT

The invention relates to an electrosurgical instrument, especially for argon plasma coagulation, with a handle (10), an outer shaft (12) that surrounds an electrode and/or an inner shaft (11, 111) and is held in the handle (10), and an actuation mechanism (13) on the handle (10) to move the outer shaft (12) in the axial direction relative to the electrode/to the inner shaft (11, 111). The invention is characterized in that the inner shaft and/or the electrode (11, 111) are mechanically connected with one another in a distal end area (65) of the outer shaft (12) in such a way that the inner shaft and/or the electrode (11, 111) can be bent by moving the outer shaft (12) relative to the inner shaft and/or to the electrode (11, 111).

13 Claims, 7 Drawing Sheets

(51) Int. Cl.
    *A61B 18/00* (2006.01)
    *A61B 17/00* (2006.01)
    *A61B 90/00* (2016.01)
(52) U.S. Cl.
    CPC ............ *A61B 2017/00309* (2013.01); *A61B 2017/00424* (2013.01); *A61B 2018/00196* (2013.01); *A61B 2018/00589* (2013.01); *A61B 2018/00607* (2013.01); *A61B 2018/00952* (2013.01); *A61B 2018/1465* (2013.01); *A61B 2090/034* (2016.02)
(58) Field of Classification Search
    CPC .... A61B 2017/00424; A61B 2090/034; A61B 2018/00589; A61B 2018/00607; A61B 2018/00952; A61B 2018/00196; A61B 2018/1465
    See application file for complete search history.

(56) References Cited

U.S. PATENT DOCUMENTS

| | | | |
|---|---|---|---|
| 6,391,027 B1* | 5/2002 | Farin | A61B 18/042 606/34 |
| 2005/0060016 A1* | 3/2005 | Wu | A61F 2/95 623/1.11 |
| 2005/0090816 A1* | 4/2005 | McClurken | A61B 17/32 606/41 |
| 2008/0051802 A1 | 2/2008 | Schostek et al. | |
| 2008/0200761 A1 | 8/2008 | Schwartz et al. | |
| 2009/0012523 A1 | 1/2009 | Ruuttu et al. | |
| 2009/0125023 A1 | 5/2009 | Stephen et al. | |
| 2010/0211076 A1 | 8/2010 | Germain et al. | |
| 2011/0098531 A1* | 4/2011 | To | A61B 17/0218 600/114 |
| 2012/0277730 A1 | 11/2012 | Salahieh et al. | |
| 2014/0171937 A1* | 6/2014 | Morris | A61B 18/042 606/34 |
| 2015/0073341 A1 | 3/2015 | Salahieh et al. | |
| 2015/0119851 A1 | 4/2015 | Hoogenakker et al. | |

FOREIGN PATENT DOCUMENTS

| | | |
|---|---|---|
| JP | 2007-504897 A | 3/2007 |
| JP | 2014-516657 A | 7/2014 |
| RU | 2299036 C2 | 5/2007 |
| SU | 466022 A | 4/1975 |
| WO | 2012040445 A1 | 3/2012 |

OTHER PUBLICATIONS

Russian Office Action dated May 22, 2019, in corresponding Russian Application No. 2016118137/14(028478), with machine English translation (19 pages).

Chinese First Office Action dated Sep. 3, 2019, in corresponding Chinese Application No. 201610312082.2, with English translation (13 pages).

European Office Action dated May 9, 2019, in corresponding European Application No. 15167061.9 (4 pages).

Japanese Office Action dated Aug. 13, 2019, in corresponding Japanese Application No. 2016-095686, with English translation (12 pages).

\* cited by examiner

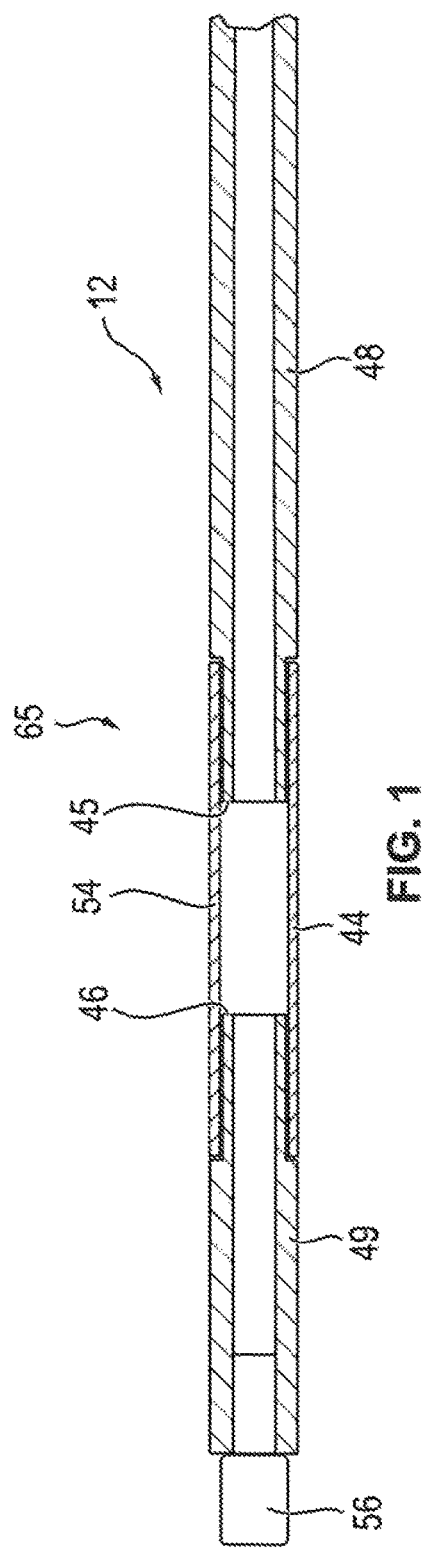
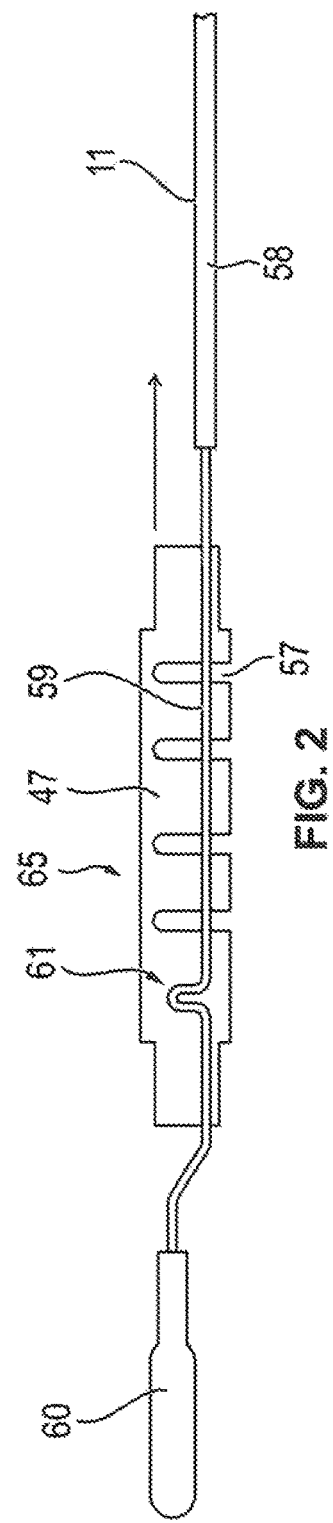
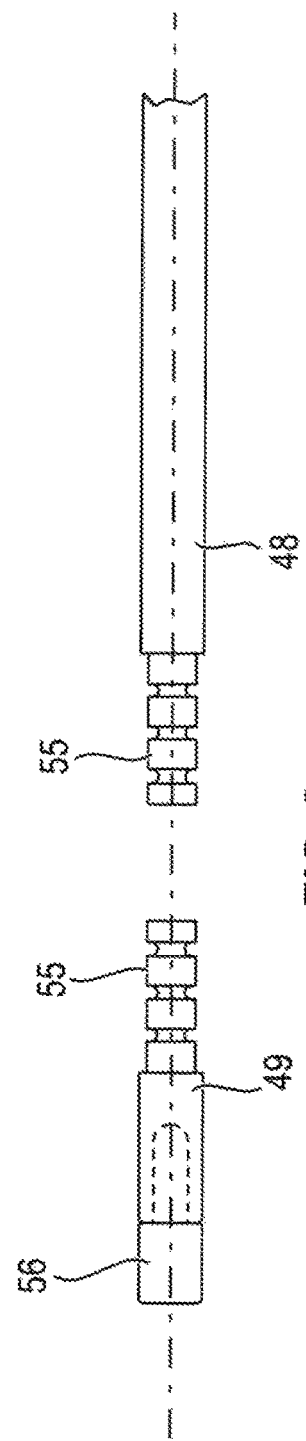

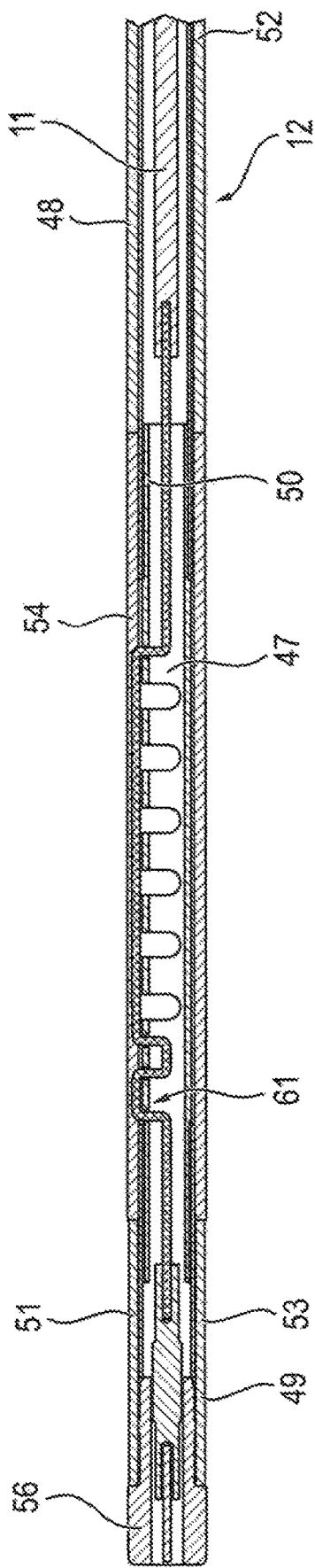
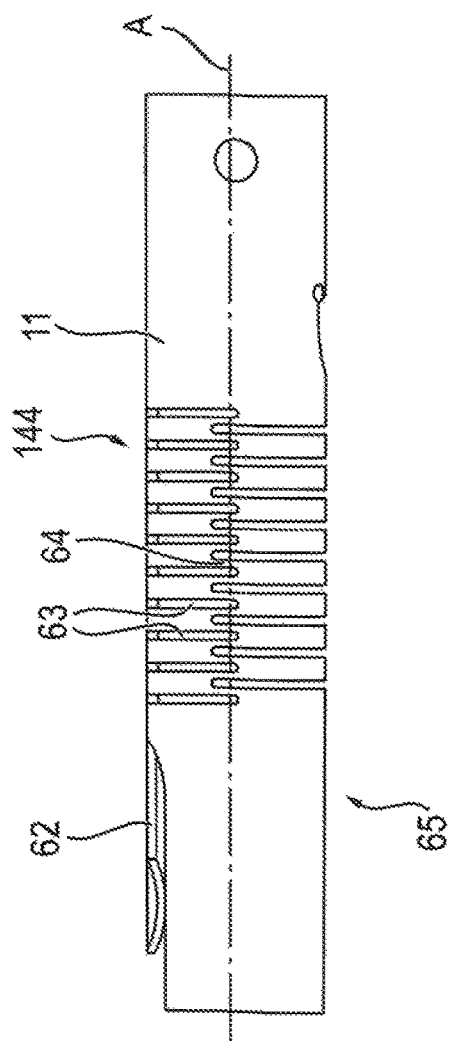
FIG. 4
FIG. 5

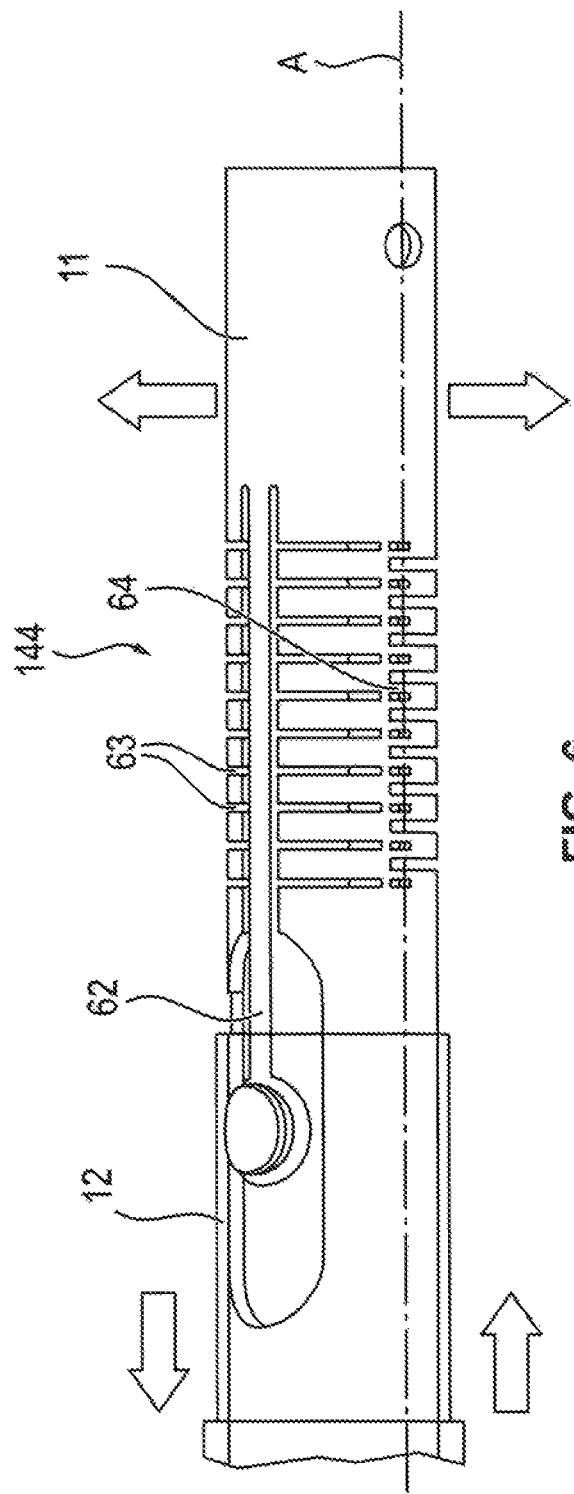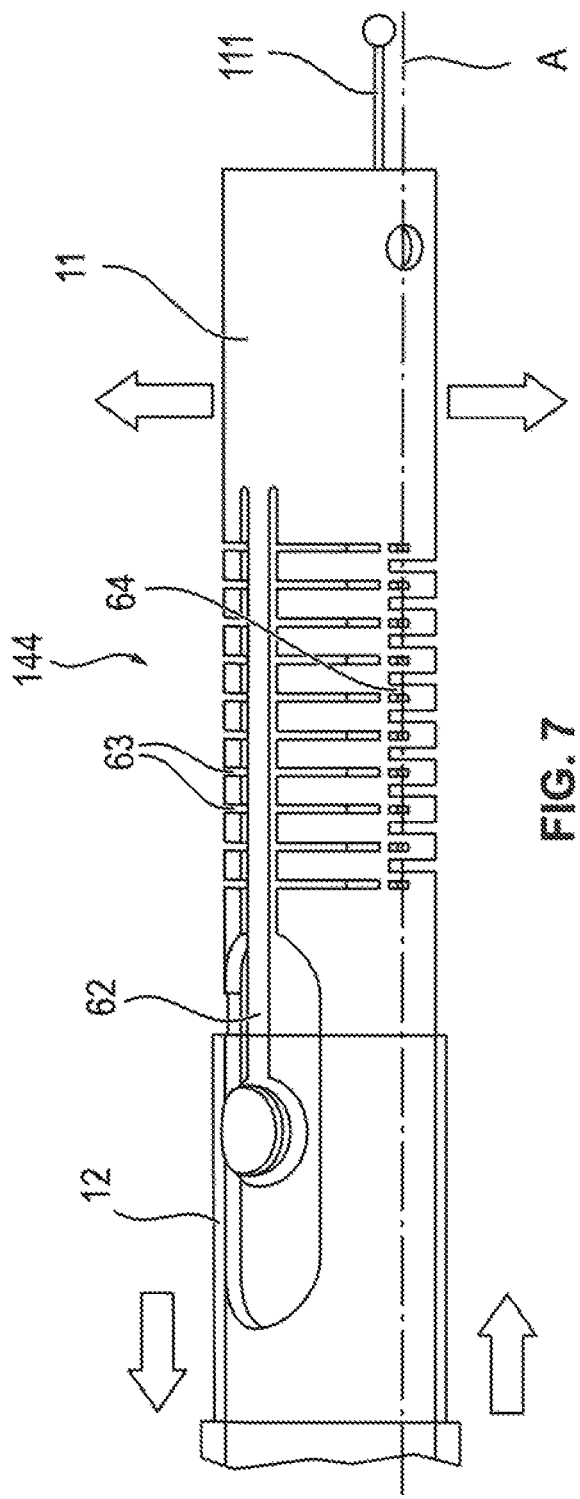

ELECTROSURGICAL INSTRUMENT AND DEVICE WITH SUCH AN INSTRUMENT

RELATED APPLICATION(S)

This application claims the benefit of European Patent Application No. EP 15167061.9 filed May 11, 2015, the contents of which are incorporated herein by reference as if fully rewritten herein.

TECHNICAL FIELD

The invention relates to an electrosurgical instrument, especially for argon plasma coagulation. The invention also relates to a device with such an instrument.

BACKGROUND

Electrosurgical instruments of the type mentioned at the beginning are used for cutting or coagulating tissue using high-frequency alternating current. Argon plasma coagulation (APC) is a special application form of electrosurgery in which high-frequency current is transferred in a contact-free manner through ionized argon gas.

The energy input is effected in the known instrument mentioned at the beginning by changing the exposed length of the electrode. To accomplish this, an axial movable outer shaft is provided that surrounds the electrode and insulates it and that can be displaced along the electrode to expose it as needed.

A central requirement on such instruments is that they allow one-hand operation. When this is done, the position of the instrument in the operating field should, to the extent possible, not change. This means that the grip should be maintained to the extent possible during operation of the instrument, even when the outer shaft is displaced.

In the instrument of the type mentioned, this is achieved by a rotating wheel that is centrally arranged in the handle of the instrument and that can be actuated with the index finger. The rotating wheel drives the outer shaft, which can, as a result, be axially displaced along the electrode.

The outer shaft of the known instrument is rigid and extends straight in the distal direction. In the case of certain applications, it is desirable for the shaft to be bent at an angle. It is true that there are APC applicators with flexible tips for this purpose. However, the tips must be manually bent at the desired angle before use. It is impossible to change the angle during use.

SUMMARY

The goal of the invention is to improve the electrosurgical instrument mentioned at the beginning to allow adjustment of the angle by actuation in the area of the handle, in particular even while the instrument is being used. Another goal of the invention is to specify a device with such an instrument.

Accordingly, the invention comprises an electrosurgical instrument, in particular for argon plasma coagulation, with a handle, an outer shaft that surrounds an electrode and/or an inner shaft, and is held in the handle, and an actuation mechanism on the handle to move the outer shaft in the axial direction relative to the electrode/to the inner shaft. The outer shaft is mechanically connected with the inner shaft/ the electrode in a distal end area of the outer shaft. The inner shaft/electrode can be bent by moving the outer shaft relative to the inner shaft/electrode.

The inventive instrument has a simple structure, since with a small number of components it achieves the functionality sought-after, namely the adjustment of an angle in the area of the tip of the shaft by actuation in the handle. Therefore, the inventive instrument is suitable as a cost-effective and thus economical disposable product.

The electrode preferably has a first, a second, and a third section, and extends out of the handle through the outer shaft. The second section of the electrode is flexible. In this embodiment, the second section of the electrode is axially fixed with the outer shaft through a sleeve. An axial movement of the outer shaft bends this outer shaft together with the second section of the electrode, and thus deflects it from its position transverse to the longitudinal axis of the shaft. The first section of the electrode is arranged proximal to the bendable area of the shaft and is connected in a stationary manner with the handle, and thus fixed to it. The first section of the electrode is rigid. The third section of the electrode is distally separated from the proximal end of the bendable area of the shaft, and thus arranged distal to the second section of the electrode. All three sections of the electrode are made as a single piece and are seamlessly connected with one another.

In this embodiment, the adjustability of the angle of the outer shaft from handle is achieved by connecting the electrode in a stationary manner with the handle and thus axially fixing it. In addition, in an area that is distally separated from the proximal end of the bendable area, a first end of the sleeve is connected in a stationary manner with the electrode, and thus axially fixed. The second end of the sleeve, which is arranged proximal to the bendable area, is fixed with the outer shaft. Moving the outer shaft changes the distance between the place where the sleeve is fixed with the electrode and the handle, specifically the distal end of the handle. Shortening this distance deflects the bendable area of the outer shaft from its straight resting position, and moves the tip of the shaft into the desired position. Doing this adjusts an angle between the tip of the shaft and the longitudinal axis of the handle or the outer shaft that projects out of the handle.

To achieve the compressing or stretching effect, the fixing of the electrode is distally separated from the proximal end of the bendable area. This deflects the bendable area in the area between the proximal end and the fixing place. The greater the distance between the proximal end and the fixing place, the longer the distance that is effective for the deflection.

It is especially favorable to fix the electrode in the area of the distal end of the bendable area, since this makes use of the entire length of the area. Here the electrode is rigid proximal to the bendable area and is fixed to the outer shaft distally separated from a proximal end of the bendable area.

It is generally understood that the electrode is not only distally fixed to the outer shaft by means of the sleeve, but is also proximally fixed with the handle in the longitudinal direction of the electrode, to support the forces that are introduced through the distal fixing of the electrode.

The bent state is generally understood to be a state in which the outer shaft is not straight along its entire exposed length, so that the tip of the shaft points in a direction that deviates from the longitudinal axis of the outer shaft projecting out of the handle. In the bent state, the proximal end and the distal end of the bendable area enclose an angle. The area between the proximal and distal end can be curved in the bent state.

The size of the angle depends on the degree of deflection of the outer shaft in the area of the bendable area, which in turn is determined by the axial movement of the outer shaft.

Pushing out the outer shaft increases the distance between the sleeve's fixing place with the electrode and the handle, so that the curved or bent area is stretched and the angle between the two sections of the shaft is reduced or completely eliminated, so that the outer shaft returns to the straight resting position.

Thus, the electrode has a double function. First, it conducts the electric current. Second, the electrode has a mechanical function, namely as a push or pull rod that transfers the tensile or compressive forces introduced from the actuation mechanism through the outer shaft, and thus causes the deflection of the bendable area. To transfer the forces in a reliable manner, the electrode in the area proximal to the bendable area is rigid. Since the electrode in the second section is flexible, the electrode follows the curvature of the bendable area.

The double function of the electrode has the advantage that it dispenses with additional mechanical components, such as, for example, traction cables.

Moreover, the invention makes it possible to maintain one-hand operation, so that the instrument can be operated in an ergonomically favorable manner.

Other preferred embodiments of the invention are indicated in the subordinate claims.

Preferably, the electrode is fixed at the distal end of the bendable area. This has the advantage that the entire length of the bendable area is used for the deflection.

The bendable area preferably has a flexible sleeve, in particular one that is longitudinally and/or transversely slit, that surrounds the electrode. The sleeve serves as a hinge for the bendable area. In an especially preferred embodiment, the electrode is connected with the sleeve to transfer compressive and tensile forces. In this case the forces introduced by the actuation mechanism through the outer shaft are transferred from the electrode to the sleeve, which is deflected out of its straight resting position and curved, due to its flexible properties in the bendable area.

A proximal end of the sleeve can be connected with a first rigid section of the outer shaft. This supports the forces introduced through the electrode, so that the sleeve is deflected by actuation of the actuation mechanism.

Preferably, the distal end of the sleeve is connected with a second rigid section of the outer shaft, which holds the third section of the electrode that serves as an ignition electrode. Thus, the bendable area is arranged between the two rigid sections of the outer shaft.

To improve the stability of the outer shaft, the first and/or the second sections of the outer shaft can each have a support tube that is connected with the sleeve on one side and with a plastic outer shaft tube on the other side.

The support tube can be a metallic support tube that has sufficient strength to accept the forces that occur during use. Thus, the support tube is connected with the sleeve on one side and with a shaft tube on the other side, and can be made of plastic. The proximal shaft tube leads to the handle. The distal shaft tube forms the second rigid shaft section, which can end, for example, in a ceramic end sleeve that is connected with the shaft tube.

Preferably, the bendable area has a hose, in particular a heat-shrink hose that forms the outer wall of the outer shaft in the area of the bendable area. This creates a gastight casing that additionally electrically insulates the electrode toward the outside. The hose is flexible, to allow the bending of the area.

Another embodiment provides that the inner shaft has a bendable area in the distal end area, and the inner shaft in this area is flexible, it being possible to bend the bendable area of the inner shaft by moving the outer shaft relative to the inner shaft.

The tensile and compressive forces for bending the inner shaft are produced by the relative motion between the outer and inner shafts. The inner shaft is connected in a stationary manner with the handle.

Preferably, the inner shaft is in the form of an electrode and serves as an electrical conductor, for example of high-frequency current for monopolar coagulation.

This makes available a bendable inner shaft that has a wide degree of freedom and that is simultaneously simple to use as an electrode, making it obsolete to provide a separate electrode.

This embodiment has the advantage that it dispenses with mounting parts to connect the electrode with the outer shaft. The lumen of the inner tube is available for the flow of media, for example for aspiration.

On the other hand, it is conceivable for an electrode to be arranged within the inner shaft. In this case, the inner shaft surrounds the electrode. When the inner shaft is bent, the electrode moves along with the inner shaft. The inner and outer shaft are electrically insulated from one another.

The inner and outer shaft can be mechanically fixed by a connection element, preferably in the area of the tip of the shaft. The connection element is preferably in the form of a band, pin, clip, or tab. The connection element is preferably flexible, and preferably made of metal.

The connection element is connected, on one side, with the outer shaft and, on the other side, with the inner shaft.

It is preferable for the connection element to be arranged in the area of the bendable area of the inner shaft, and even more preferable for it to be arranged distal to the bendable area of the inner shaft, and thus for it to bridge the bendable area of the inner shaft.

The bendable area of the inner shaft can have slits in the corresponding wall section. The special arrangement of the slits allows the inner shaft to accept forces in the axial direction and to bend transverse to the longitudinal axis of the inner shaft.

On the other hand, the bendable area of the inner shaft can be formed by opposite slits. These slits are preferably formed by a laser beam cutting process.

Each of the slits extends beyond the axial middle of the inner shaft, so that a type of bent straw effect is achieved. In this case, the opposite slits are offset with respect to one another and overlap in the area of their respective tips.

It is conceivable for the tips of the respective slits to overlap only slightly, and therefore for there to be a small degree of overlap. The degree of overlap can be selected in such a way to ensure the stability of the inner shaft and simultaneously allow a sufficient bend angle.

It is preferable for the slits to be arranged with equal distances to one another in the longitudinal direction of the inner shaft, which allows a uniform bending of the inner shaft.

The slits are preferably designed like [the teeth of] a comb, the offset of the slits allowing a type of meshing of the opposite slits.

The greater the overlap in the overlap area, the greater the spring travel of an individual element. Therefore, greater overlap leads to a smaller restoring force.

The more slits are made in the tube, the greater the angular range in which the inner shaft can be bent in the bendable area. Moreover, the greater the width of the slit is, the greater the angular range for the same number of slits.

The area in which the slits overlap describes a spring geometry wherein the inner shaft is not plastically deformed, but rather the resulting spring elements allow an elastic deformation of the inner shaft.

The width of the bridges may not be chosen to be too large, since otherwise the elastic deformation becomes a plastic deformation, and the inner shaft can be destroyed.

The connection element is preferably an integral part of the inner shaft and is arranged outside the axial middle, so that the mechanical connection between the outer shaft and the inner shaft allows a force due to the relative motion between the outer shaft and the inner shaft to be transferred through the connection element.

The force acts outside the axial middle. The force shortens the path on the side of the connection element and the inner shaft bends in the direction of the connection element.

In a preferred embodiment, the handle has a braking device that exerts a braking force on the outer shaft. The actuation mechanism forms a rotating wheel with a step-up gear that is connected with the outer shaft to transfer the compressive force.

The security of the instrument against unwanted movement of the tip of the shaft, for example when it is used together with a trocar, is improved by the braking device. The braking force exerted by the braking device on the outer shaft prevents the latter from being pushed in the proximal direction during use, for example when it is introduced through a trocar.

Thus, the braking force leads to self-locking of the outer shaft, securing the latter against unwanted displacement. This avoids unwanted movement of the tip of the shaft.

To change the angle of the tip of the shaft, an actuation force can be applied to the outer shaft by actuating a rotating wheel. This force is usually applied by the finger of the user. The resistance of the rotating wheel lies in a range that is perceived to be ergonomically comfortable. This makes it easy and safe for the user to [operate] the instrument, in particular to bend the shaft. In addition, in this embodiment the instrument has a step-up gear that is formed by the actuation mechanism and that is connected with the outer shaft to transfer the compressive force. The step-up gear balances the braking force applied by the braking device, so that the rotating wheel or generally the actuation mechanism is easy to operate.

The outer shaft can be non-rotatably or rotatably mounted in the handle. If the outer shaft is mounted in the handle so that it is rotatable in the peripheral direction, the position of the bent tip of the shaft can be changed by rotating the shaft. This makes it easy to change the application position when the outer shaft is bent.

It goes without saying that the rotating wheel can be rotated in two directions (clockwise/counterclockwise), so that the outer shaft can be moved in the distal direction and in the proximal direction.

In summary, in this embodiment the instrument's safety is improved, since the outer shaft is secured by the braking device against unwanted displacement. The instrument's ease of operation is simultaneously maintained, since the actuation mechanism forms a step-up gear that converts the finger power applied by the user into the compressive force acting on the outer shaft. The step-up gear acts as a lever arrangement that increases the compressive force in comparison with that of the fingers.

To increase the leverage more, the rotating wheel can have a lever-like projection that extends radially starting from the outer periphery of the rotating wheel and that can be actuated with the finger.

Preferably, the rotating wheel comprises a drive gear and at least one driven gear that is non-rotatably connected with the drive gear and that is connected with the outer shaft to transfer the compressive force. The diameter of the driven gear is smaller than that of the drive gear. This achieves, in a simple way, the step-up required for easy actuation of the outer shaft. Another advantage of this embodiment is the cost-effective and reliable design it offers.

The actuation mechanism can comprise a carriage that is axially movable in the thrust direction and that is connected on one side with the outer shaft and on the other side with the step-up gear. This creates a robust and simple design that securely transfers the drive force applied by the user to the outer shaft.

The carriage can have at least a first gear rack that is arranged parallel to the thrust direction and that engages with the driven gear. This embodiment allows simple and reliable conversion of the rotational movement of the rotating wheel into a linear movement of the outer shaft.

To improve the transfer of force, the carriage can have a second gear rack parallel to the first one, the drive gear being arranged between the two gear racks and non-rotatably connected with another driven gear. The other driven gear meshes with the second gear rack.

The handle preferably has a holding plate with a linear guideway in which the carriage is arranged so that it can move in the axial direction. The linear guideway has at least one opening, in particular two parallel openings, for the carriage. The holding plate allows a compact structure, which requires little space to support the carriage.

The braking mechanism can have a clamping element, in particular a clamping ring, that is held in the handle and applies the braking force to the outer shaft. The clamping element forms a passive means of braking that allows the instrument to have a simple and cost-effective structure.

In a preferred embodiment, the actuation mechanism has a stop device with which the outer shaft can be fixed in at least one position, in particular in a completely extended position. The stop device is especially suitable for trocars, which produce an especially large resistance when the instrument is introduced, such as, for example, reusable trocars with a butterfly valve. The stop device is used to fix the outer shaft in addition to the braking mechanism, so that greater axial forces can be transferred from the outer shaft, without the latter being displaced relative to the electrode.

This stop device can comprise at least one first means of latching that is arranged on the carriage. A second means of latching is arranged on the handle, in particular on the holding plate, and can be connected with the first means of latching to fix the outer shaft. The two means of latching have the advantage that they are simple to produce, for example by injection molding, and simultaneously allow secure fixing of the outer shaft.

In an especially preferred embodiment, the electrode and the outer shaft are arranged so that each of them can rotate about its longitudinal axis relative to the handle.

The electrode is guided by a sliding sleeve that connects the outer shaft and the electrode in a non-rotatable and axially movable manner.

This embodiment is suitable for electrodes that are not rotationally symmetric, such as, for example, spatula electrodes, or can be used when the outer shaft is bent to change the application position by rotation about the shaft's longitudinal axis. This makes it simple to orient the electrode in the peripheral direction. This embodiment has the advantage that rotation of the electrode is also possible when the instrument is located in the trocar. In this embodiment, the rotation is introduced by the outer shaft, which is non-rotatably connected with the electrode through the sliding sleeve. The sliding sleeve has the additional function of producing the relative mobility between the outer shaft and the electrode. To accomplish this, the sliding sleeve connects the outer shaft and the electrode in a non-rotatable and axially movable manner. Since the outer shaft projects out of the handle, no additional components are required to rotate the electrode. The user simply grasps the outer shaft and rotates it together with the electrode.

At least sections of the sliding sleeve can have a profiling on the inner periphery that positively interlocks with the electrode, at least sections of which are correspondingly profiled, to transfer a torque. This embodiment is cost-effective and secure, since a correspondingly profiled sliding sleeve is simple to make and the positive interlocking transfers torque in a secure manner.

A cost-effective and simple structure is preferably achieved by the sliding sleeve and the carriage being rotationally movable and solidly connected in the axial direction of the sliding sleeve to transfer the compressive force. The carriage has a retaining ring that surrounds the sliding sleeve around at least part of its periphery.

The invention is explained in detail below with further details and with reference to the attached schematic figures. The figures are as follows:

BRIEF DESCRIPTION OF THE DRAWINGS

FIG. 1 a longitudinal section of the outer shaft according to one inventive sample embodiment;

FIG. 2 a longitudinal section through the mounting parts of the outer shaft, in particular the sleeve and electrode;

FIG. 3 a side view of the rigid shaft section;

FIG. 4 a longitudinal section through the outer shaft of an inventive sample embodiment of an instrument in the area of the bendable area;

FIG. 5 a side view of the inner shaft of the instrument;

FIG. 6 a perspective side view of the inner shaft of the instrument shown in FIG. 4 with the outer shaft;

FIG. 7 a perspective side view of the inner shaft of the instrument shown in FIG. 5 with the electrode;

FIGS. 1 through 8 show a sample embodiment of an electrosurgical instrument that can be used for working on biological tissue, for example for argon plasma coagulation.

DETAILED DESCRIPTION

Figure 8:
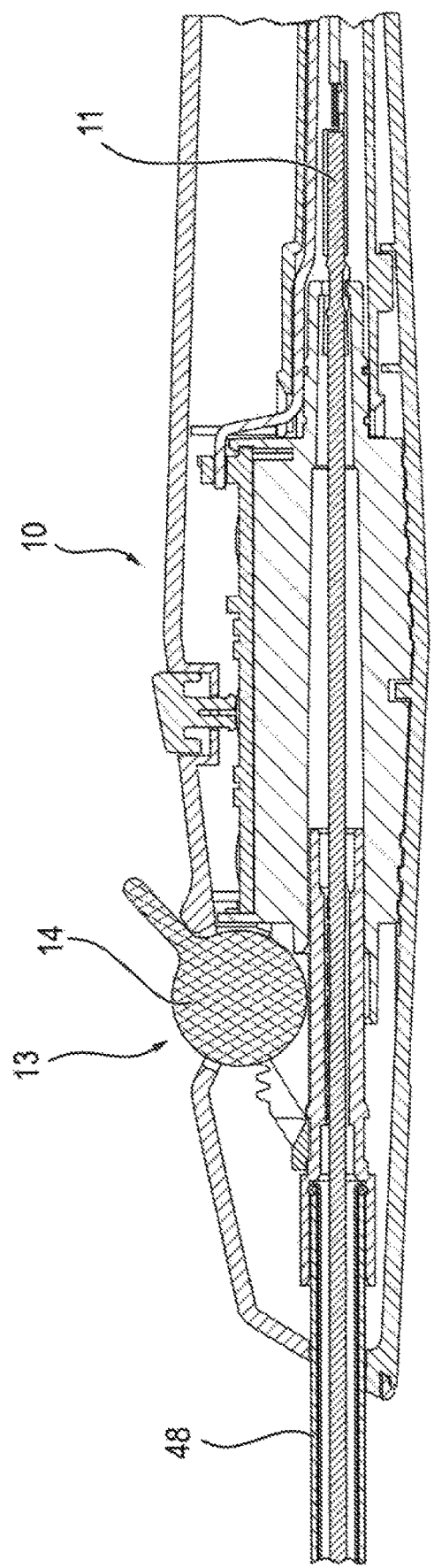
FIG. 8 a longitudinal section through the handle of the instrument shown in FIG. 4.

The invention is not limited to instruments for argon plasma coagulation, but rather can generally be used for instruments in the area of electrosurgery, in which a tip of the shaft is actively moved, i.e., from the handle.

The electrode 11 of the sample embodiment can be, e.g., a hollow electrode that has a gas channel (APC electrode). Other electrodes are possible.

FIGS. 1 through 3 show various components of the instrument in the disassembled state, which are connected with the bending of the outer shaft 12 in the area of the tip of the shaft, which is controlled from handle 10.

FIG. 1 shows the distal end area 65 of the instrument's outer shaft 12 in the area of the tip, without the mounting parts in the outer shaft that are provided in the installed state. In the area of the tip, the outer shaft comprises a first and second rigid shaft section 48, 49, which is shown with more details in FIG. 3. The bendable area 44 is arranged between the two rigid sections. A proximal end 45 of the area 44 is connected with the first, proximal shaft section 48, and a distal end 46 of the area 44 is connected with the second, distal shaft section 49.

The bendable area 44 acts as a joint, and has the function of allowing relative motion between the first and second shaft sections 48, 49, so that an angle can be set between the first shaft section 48 and the second shaft section 49.

To accomplish this, the bendable area has a hose 54 that connects the two rigid shaft sections 48, 49. The hose 54 is flexible. The hose 54 forms the outer wall of the outer shaft 12 in the area of the bendable area 44. It is advantageous for the hose 54 to be in the form of heat-shrink hose, in particular silicone heat-shrink hose, which facilitates assembly and achieves a gastight connection between the hose 54 and the two shaft sections 48, 49. Other mechanical connection elements between the two shaft sections 48, 49 are possible instead of the hose.

Figure 9:
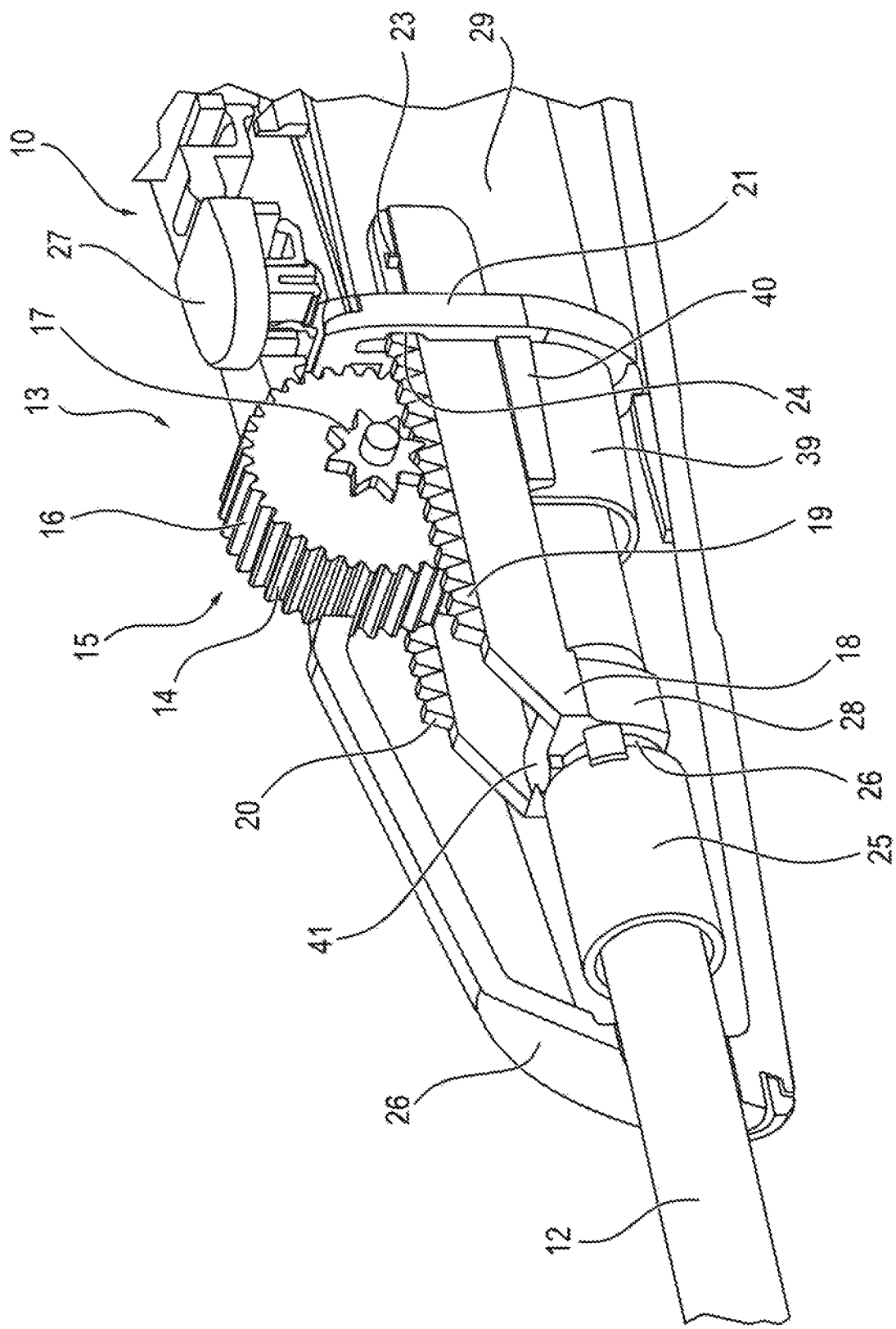
FIG. 9 a perspective view of an inventive sample embodiment of the instrument in which the housing has been partly removed.

The proximal first shaft section 48 is connected with the handle (see FIG. 9).

To connect the distal end of the first shaft section 48 with the hose 45, the first shaft section 48 can have a profiled end piece 55 that is connected with the hose 54 (FIG. 3). The second distally arranged shaft section 49 also has a profiled end piece 55 for the hose 54 at the proximal end. At the distal end of the rigid shaft section 49, there can be a ceramic end sleeve 56 in whose area the ignition electrode is arranged; the ignition electrode can be made of tungsten wire, for example.

Instead of the one-part embodiment of the two shaft sections 48, 49 shown in FIG. 1, they can be made in multiple parts and each have a support tube 50, 51 that is arranged between the hose 54 and a shaft tube. The support tubes 51, 50 or sleeves improve the stability of the outer shaft and are made of metal. The outer shaft tubes 52, 53, which are connected with the support tubes 51, 50, are made of plastic.

In the assembled state, the mounting part shown in FIG. 2 is located in the area of the bendable area 44, as shown in FIG. 4. The mounting part shown in FIG. 2 comprises the electrode 11 and a sleeve 47, which surrounds thee electrode. The sleeve 47 is made of a flexible material and has multiple transverse slits 57 that extend transverse to the longitudinal extension of the sleeve 47. To improve the flexibility further and to hold the electrode in the bent state, the sleeve 47 can have a longitudinal slit (not shown).

The electrode 11 forms three sections. The first section 58 is rigid, for example made of a steel wire with a diameter of about 1.5 mm. In the installed position, the first rigid section 58 is located proximal to the bendable area 44. Distal to the rigid section 58 there is a second flexible section 59 that is made, for example, of spring steel wire with a diameter of about 0.5 mm. In the installed position, the second flexible section 59 is located in the bendable area of the shaft; its flexibility allows deflection of the bendable area 44 when the actuation mechanism on the handle 10 is actuated.

In addition, the electrode 11 is fixed. The fixing is achieved by the electrode 11 being mechanically connected with the sleeve 47 being able to transfer tensile and compressive forces. The electrode 11 is connected with the sleeve 47 at a fixing place 61 that is distally separated from the proximal end 45 of the bendable area 44. In the example shown in FIG. 2, the fixing place 61 is located in the area of the distal end 46 of the bendable area 44, when it is in installed position. The result is that when the outer shaft is displaced the entire length of the bendable area 44 can be used for deflection. It is possible to offset the fixing place in the proximal or distal direction.

The connection in the area of the fixing place 61 can be a positive interlocking connection, as shown in FIG. 2. Other types of connection are possible. In the example shown in FIG. 2, the electrode 11 is curved in an arch and engages into the sleeve 47. In other words, in the area of the fixing place 61 the electrode 11 forms a hook-shaped connection that is anchored with the sleeve 47. This the transfers the forces in a secure manner.

Distal to the second flexible section 59 of the electrode 11 there is a third end section 60 in whose area the ignition electrode is arranged. This electrode can be made, for example, of tungsten wire having a diameter of about 0.5 mm.

FIG. 2 does not show that in addition to the fixing place 61, the proximal end or proximal area of electrode 11 is axially arranged and fixed in a stationary manner in a handle 10.

The installed state is shown in FIG. 4. In this figure it can be seen that the sleeve 47 is arranged in the area of the bendable area 44 and that it is radially surrounded on the outside by hose 54. One difference from the example shown in FIG. 2 is the design of the fixing place 61, which in FIG. 4 has a multiple curvature to improve anchoring. In contrast to the prior art, the sample embodiments in FIGS. 1 through 5 do not allow relative motion between the tip of the outer shaft and the electrode to expose the electrode. Thus, the instrument shown in FIGS. 1 through 5 is most suitable for coagulation.

FIG. 5 shows another embodiment in which the electrode 11 is in the form of an inner shaft 11 and has a bendable area 144 in a distal end area 65.

The bendable area 144 is formed by slits 63, which are formed, for example, by laser cutting in the inner shaft 11. The slits 63 are separated from one another by 0.2 mm, for example, the slit width being between 0.1 and 1.0 mm.

In the axial middle A of the inner shaft 11, the slits 63 are arranged in an overlapping manner. This overlapping area 64 between the opposite slits 63 is 0.3 to 0.8 mm, for example, especially preferably 0.6 mm.

FIG. 5 also shows, in the distal end area 65 of the inner shaft 11, a connection element 62 in the form of a clip that is an integral part of the inner shaft 11. The connection element 62 is preferably formed by laser cutting, even more preferably [if it is formed] together with the slits 63. This allows simple and cost-effective manufacturing. The connection element 62 is mechanically connected with the inner shaft 11 in the bendable area 144, or distal to the bendable area 144.

FIG. 6 shows the design of the inner shaft 11 described with reference to FIG. 5, the inner shaft 11 in FIG. 6 being shown connected with the outer shaft 12 by the connection element 62.

The inner shaft 11 and the outer shaft 12 are connected by the connection element 62 in such a way that moving the outer shaft 12 relative to the inner shaft 11 exerts a force on the inner shaft 11 through the connection element 62 such that the inner shaft 11 changes its orientation in the bendable area 144 and is deflected.

The inner shaft 11 is preferably bent perpendicular to a plane that is defined by the axial middle A of the inner shaft 11 and the overlapping areas 64. Bending of the inner shaft 11 in this plane is prevented by the arrangement of the slits 63.

FIG. 7 shows the case in which an electrode 111 is provided in addition to the inner shaft 11. Thus, in this case the inner shaft 11 does not serve as an electrode, as is the case in the embodiments described with reference to FIGS. 5 and 6, but rather the inner shaft surrounds an electrode 111. The electrode 111 can be of various forms. It can be in the form of a needle electrode, a spatula electrode, or a sleeve, as a projection of the inner shaft 11, or it can be of another form. The inner shaft 11 can be in the form of a means of contact with the electrode. Alternatively, the electrode 111 can also extend all the way through the inner shaft 11 into the handle 10, and be connected there with the electrical supply.

FIG. 8 shows how the actuation mechanism 13 is connected with the rotating wheel 14. FIG. 8 and FIG. 4 belong together in that the handle 10 shown in FIG. 8 is the continuation of the outer shaft 12 shown in FIG. 4. The mechanism to convert the torque on the handle 10 into the translational motion of the outer shaft 12 is explained in detail in FIGS. 9 through 11 and is disclosed in connection with the sample embodiment shown in FIGS. 1 through 4 and 8.

The electrode 11 is mounted in the handle 10 so that it is stationary. The handle 10 has connections or lines for the electrode that allow the supply of power and possibly gas to the electrode 11. In addition, the handle has one or more means of actuation, for example push buttons 27, on it. The electrode 11 is arranged in a movable outer shaft 12, that projects beyond the handle in the distal direction and is held in the housing 26 of the handle 10 (see FIG. 9). The outer shaft 12 is made out of an insulating material and surrounds the electrode 11 at least in the area outside the handle 10.

The outer shaft 12 is movable relative to the electrode 11, so that the orientation of the tip of the instrument can be adjusted by an axial movement of the outer shaft 12.

The instrument has a braking device that continually applies a braking force to the outer shaft 12 and acts as a displacement safeguard. The braking force or self-locking of the outer shaft 12 counteracts the force of resistance when the instrument is introduced into a trocar, and prevents unwanted displacement of the outer shaft 12 in the proximal direction. The advantage of the displacement safeguard of the outer shaft 12 also comes in useful in other situations, for example in dissection.

Figure 11:
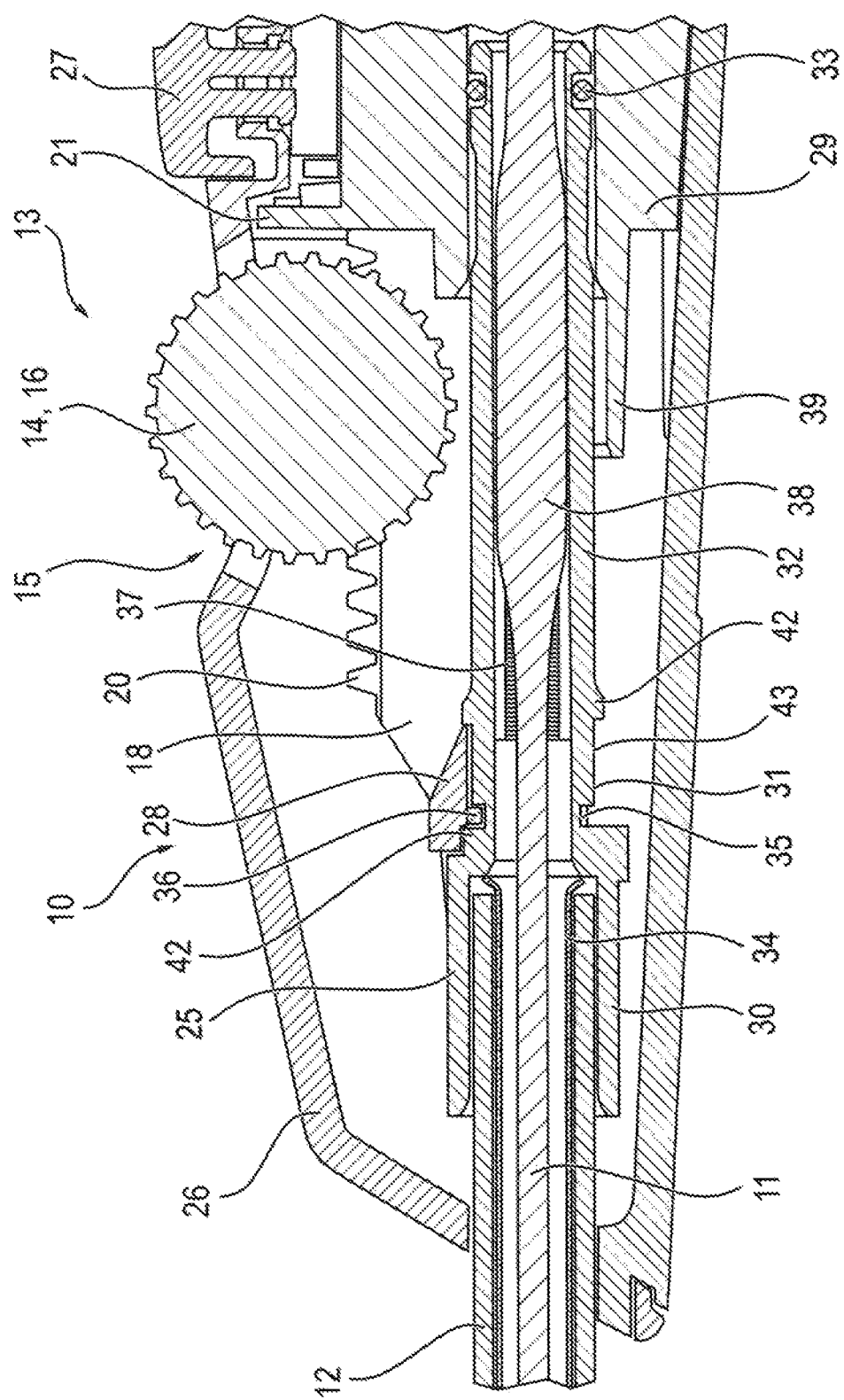
FIG. 11 a longitudinal section of the instrument shown in FIG. 6 along the central axis.

Specifically, the braking device has a friction-based clamping element, for example in the form of a clamping ring 33 (FIG. 11). The clamping ring 33 can be an O-ring. Other passive means of braking that counteract the force of resistance in the trocar are possible. The clamping ring 33 is at least indirectly connected with the outer shaft 12 and transfers the axial forces introduced into the outer shaft 12 to the handle 10, specifically to the housing 26 of the handle 10. To accomplish this, the outer shaft 12 is connected with a sliding sleeve 25. The sliding sleeve 25 and the outer shaft 12 are coaxially arranged. The sliding sleeve 25 can be understood to be an axial extension of the outer shaft 12 into the handle 10. At the distal end of the sliding sleeve 25, the clamping ring 33 is arranged in a suitable matching groove in such a way that the clamping ring 33 sticks out over the outer periphery of the sliding sleeve 25. The clamping ring 33 is supported in the handle 10 and produces a braking force that counteracts a longitudinal force acting on the outer shaft 12, for example the force of resistance in the trocar.

Specifically, the sliding sleeve 25 is coaxially arranged in an inner sleeve 29 that is solidly connected with the housing 26, in particular by a holding plate 21. The clamping ring 33 presses against the inner periphery of the inner sleeve 29, producing an axial braking force. The inner sleeve 29 simultaneously forms the axial guideway of the sliding sleeve 25.

The clamping ring 33, or generally speaking the braking device, can be arranged at another place on the sliding sleeve 25. It is also possible to use more than one clamping ring 33, for example two clamping rings.

To keep the braking device from making it difficult to operate the instrument, the actuation mechanism 13 forms a step-up gear 15 that is connected with the outer shaft 12 to transfer the compressive force.

The actuation mechanism 13 has a rotating wheel 14 that at least partly projects out of the housing 26 of the handle 10, so that part of the periphery of the rotating wheel 14 is accessible for the actuation by a finger. The rotation of the rotating wheel 14 causes axial displacement of the outer shaft 12. Clockwise or counterclockwise actuation of the rotating wheel 14 can advance the outer shaft in the distal direction, or pull it back in the proximal direction. In other words, the outer shaft 12 can be moved back and forth.

The function of the step-up gear 15 is to convert the torque introduced into the rotating wheel 14 so as to apply an increased compressive force to the outer shaft. The step-up gear 15 is adapted so that the finger force to actuate the rotating wheel 14 is smaller than the self-locking of the outer shaft 12.

The step-up gear 15 comprises the rotating wheel 14, which in turn has a drive gear 16 and at least one driven gear 17 that is non-rotatably connected with the drive gear 16 (FIG. 9). The driven gear 17 is in the form of a gear that is coaxially connected with the drive gear 16. The drive gear 16 can have means of holding for secure movement, for example in the form of ribs on the outer periphery. This ensures precise movement of the drive gear 16 by means of a finger. The rotating wheel 14 can be in the form of a step gear, the drive gear 16 and the driven gear 17 being made as a single piece or integral. Alternatively, the drive gear 16 and the driven gear 17 can be mechanically connected with one another.

The rotating wheel can have a projection on it in the form of a finger lever.

As can easily be seen in FIG. 9, the diameter of the drive gear 16 is greater than that of the driven gear 17. Specifically, the outside diameter of the drive gear 16 is about 2.8 times larger than that of the driven gear 17. Thus, the [mechanical advantage] is about 1:2.8.

Thus, the required finger force is about 2.8 times smaller than the self-locking of the outer shaft 12.

The [mechanical advantage] can be in the range of 1:2.6-3.0, especially in the range 1:2.7-2.9.

Another advantage of the step-up gear is that the travel or circular measure covered on the outer periphery of the drive gear 16 is also 2.8 times or another multiple of the travel of the outer shaft 12. This allows especially exact adjustment of the shaft angle.

In this sample embodiment, the outside diameter of the drive gear 16 is about 12.5 mm. The braking force or clamping force required for self-locking of the movable outer shaft 12 is about 4 newtons.

The conversion of the torque applied from the rotating wheel 14 into a translational thrust motion of the outer shaft 12 is achieved by a carriage 18, which is axially movable in the proximal and distal direction. The carriage 18 forms the connection between the outer shaft 12 and the step-up gear 15. To accomplish this, the carriage 18 has a first gear rack 19 that is arranged parallel to the thrust direction of the outer shaft 12. The first gear rack 19 meshes with the driven gear 17. Other designs for converting the rotation into a translational motion are possible. In the example shown in FIG. 9, the gear rack 19 is arranged on the outside. Alternatively, it is possible to provide a gear rack that lies on the inside of a longitudinal slit that extends parallel to the central axis of the electrode 11. The driven gear 17 is then arranged inside the longitudinal slit.

As can be seen in FIG. 9, the carriage 18 has a second gear rack 20 that is arranged parallel to the first gear rack 19. The drive gear 16 is arranged between the two gear racks 19 and 20 and is non-rotatably connected with another driven gear 17. The other driven gear 17 (not shown) engages with the second gear rack 20. The symmetrical structure of the actuation mechanism 13 introduces force uniformly and improves the instrument's safety.

Figure 10:
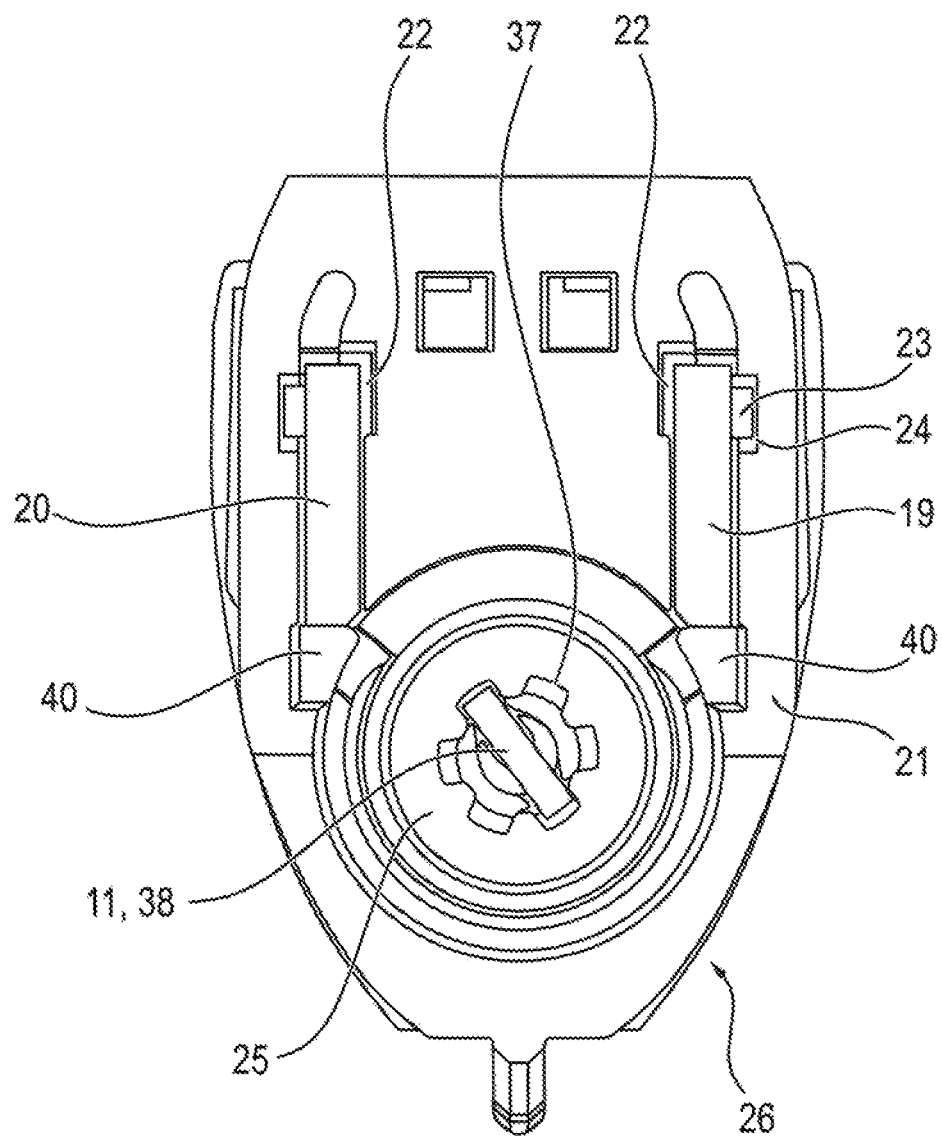
FIG. 10 a cross section of the instrument shown in FIG. 6, wherein the rotating wheel is omitted.

The two gear racks 19, 20 form two arms that extend parallel to the longitudinal axis of the electrode 11 and/or of the outer shaft 12. The two gear racks 19, 20 are arranged in a linear guideway that is formed by the holding plate 21. The holding plate 21 sits tightly in the housing 26 and has two parallel openings 22 for the carriage 18 (FIG. 10). The gear racks 19, 20 pass through the two openings 22, so that secure translational motion of the carriage 18 is possible. The rotating wheel 14 is arranged between the two gear racks 19, 20 in front of the holding plate 21, which gives the handle 10 a compact structure.

Es it is also possible to provide a single gear rack, e.g., only the first gear rack 19.

Another improvement in safety is achieved by a stop device on the carriage 18. The stop device fixes the outer shaft 12 in a specified position, in particular in the position in which the outer shaft 12 and the electrode are arranged straight and stretched out in the longitudinal direction. The stop device can comprise means that ensure self-locking of the movable outer shaft 12. This makes it possible to fix various bent positions of the distal end of the instrument.

In contrast to the stop device, which fixes the carriage 18 in a certain position, the braking device acts in every position of the carriage 18, so that infinitely variable adjustment of the outer shaft 12 is possible.

Specifically, the stop device has a first means of latching 23 that is arranged at the proximal end of each of the first and second gear racks 19, 20.

In the latched state, the first means of latching 23 interacts with a second means of latching 24 that is formed on the handle 10. Specifically, the second means of latching 24 on the holding plate 21 is in the form of a latching hole. The first means of latching 23 can be a correspondingly formed latch lug that is arranged on the side of the two gear racks 19, 20.

The stop device improves the instrument's overall safety.

It is also possible to use the stop device independently of the step-up gear and the braking device, for example when the instrument is intended to be used exclusively with trocars having a very high force of resistance, such as, e.g., in reusable trocars with a butterfly valve.

Another advantage of the instrument is that the electrode 11 can be rotated or oriented in the peripheral direction, even when the outer shaft 12 is at least partly inserted into a trocar. To accomplish this, the electrode 11 and the outer shaft 12 are arranged so that each of them can rotate about its longitudinal axis relative to the handle. In other words, the electrode 11 and the outer shaft 12 can be twisted together. To accomplish this, the sliding sleeve 25 is provided, through which the electrode 11 is guided. The sliding sleeve 25 connects the outer shaft 12 and the electrode 11. This is a non-rotatable and axially movable connection. Thus, the sliding sleeve 25 allows the transfer of a torque from the outer shaft 12 to the electrode 11. The sliding sleeve 25, and thus the outer shaft 12, which is connected with it so that it is coaxial or aligned with it, can simultaneously be axially displaced relative to the electrode 11, which allows bending in the area 44.

This double function (torque transfer and axial displacement) is achieved by the fact that the sliding sleeve 25 has, at least in sections, a profiling 37 on the inner periphery. The electrode 11 is correspondingly profiled in the area of the profiling 37 and engages in a positive interlocking manner with the sliding sleeve 25 to transfer the torque. The positive interlocking connection is formed so that the sliding sleeve 25 can be moved along the electrode 11 both in the distal and also in the proximal direction.

Specifically, the sliding sleeve 25 has at least three sections, namely a distal sleeve section 30, a middle sleeve section 31, and a proximal sleeve section 32. The profiling 37 is formed in the area of the proximal sleeve section 32. The braking device, specifically the clamping ring 33 is arranged on the proximal end of the proximal sleeve section 32. The profiling 37 extends over a length that approximately corresponds to the length of the two gear racks 19, 20. This means that the positive interlocking connection between the electrode 11 and the profiling 37 is maintained in every relative position of the sliding sleeve 25, so that the rotation function is present, independent of the respective position of the outer shaft 12.

As is shown in FIG. 10, the profiling 37 is a type of spline profile. This makes it easier to assemble, since the correspondingly profiled electrode 11 can be pushed into the sliding sleeve essentially independently of its rotational position. The electrode 11 has a profile section 38 with a rectangular cross section, as is shown in FIG. 10. The proximal and distal end of the profile section 38 of the electrode 11 each taper, as shown in FIG. 11. Distal and proximal to the profile section 38, the electrode conventionally has an essentially circular cross section. At the distal end of the electrode, the cross section can change into one that is not rotationally symmetric. The electrode can be, e.g., a spatula electrode.

The middle sleeve section 31 has a shoulder 42 in both the distal and proximal directions. Between the two shoulders 42, a stop area 43 is formed that is rotatably connected with the carriage 18. The stop area 43 forms a recess between the two shoulders 42. This recess has a retaining ring 28 of the carriage 18 arranged in it. The retaining ring 28 is partly open, and surrounds the sliding sleeve around only part of its periphery, so that for assembly the retaining ring 28 can simply be clipped onto the sliding sleeve 25. The retaining ring 28 abuts the two shoulders 42, so that axial forces or the compressive force in the proximal and distal direction can be transferred to move the outer shaft 12. As another safety [measure], the middle sleeve section 31 has an annular groove 35 that has a carrier 36 of the retaining ring 28 engaged in it. The carrier 36 and the annular groove 35 can rotate relative to one another, so that the sleeve 25 can rotate freely in the retaining ring 28. The carrier 36 also transfers the compressive force in both axial directions.

The retaining ring 28 is arranged between the two gear racks 19, 20 at their distal end. Specifically, a transverse bar 41 is provided that connects the distal ends of the two gear racks 19, 20, as is shown in FIG. 9. The transverse bar 41 in turn is solidly connected, or made as a single piece with, the retaining ring 28. The transverse bar 41 and the retaining ring 28 can also as be considered to be a transverse bar with two jaws arranged beneath it that surround the sliding sleeve 25 around part of its periphery.

A sufficient distance is provided between the transverse bar 41 and the holding plate 21, so that the carriage 18 can be moved past the rotating wheel 14 without colliding with the rotating wheel 14.

The sliding sleeve 25 also comprises a distal sleeve section 30. The distal sleeve section 30 is non-rotatably connected with the outer shaft 12. The connection can be mechanical, for example provided by a fastening sleeve 34 that is arranged in the outer shaft 12 and is crimped with the sliding sleeve 25 at the proximal end of the outer shaft 12. Other fastening possibilities are conceivable. The distal sleeve section 30, together with the housing 26, forms an axial stop that determines the position of maximum withdrawal of the outer shaft 12.

To support the linear guideway of the carriage 18, the handle has the above-mentioned inner sleeve 29 that is solidly connected with the holding plate 21. The inner sleeve 29 is arranged coaxial to the electrode 11, and extends distal and proximal to the holding plate 21, as is shown in FIGS. 9, 11. On the distal side of the holding plate 21, the inner sleeve 29 forms a sleeve section 39 with two guide bars 40 that extend parallel to the central axis of the inner sleeve 29. The guide bars 40 form support surfaces for the two gear racks 19, 20 and so improve the stability of the linear guideway.

As is shown in FIG. 11, part of the peripheral wall of the inner sleeve 29 is removed in the area of the rotating wheel 14, to create space for the rotating wheel 14, which is arranged in housing 26 except for the peripheral segment required for finger actuation, so that it does not collide with the inner sleeve 29. This contributes to a compact structure of the handle.

The rotation function of the handle makes it suitable for positioning the bent electrode 11, so that the handle is not only especially secure and cost-effective, but rather easy to operate.

In summary, the instrument combines three functions:

From the handle, the actuation mechanism bends the tip of the shaft and the third section of the electrode, so that the angle of the tip of the shaft and the electrode can be changed during use. The outer shaft and thus the electrode can be rotated about their longitudinal axis, so that the electrode can be oriented, which is advantageous in electrodes that are not rotationally symmetric, that is, to change the application position. The braking device prevents unwanted changes in the position of the tip of the shaft, e.g., when the outer shaft is moved in a trocar.

The inventive instrument is additionally disclosed and claimed also in connection with an electrosurgery device, in particular for use on biological tissue, for example for argon plasma coagulation.

LIST OF REFERENCE NUMBERS

10 Handle
11 Electrode, inner shaft

12 Outer shaft
13 Actuation mechanism
14 Rotating wheel
15 Step-up gear
16 Driving gear
17 Driven gear
18 Carriage
19 First gear rack
20 Second gear rack
21 Holding plate
22 Opening
23 First means of latching
24 Second means of latching
25 Sliding sleeve
26 Housing
27 Push button
28 Retaining ring
29 Inner sleeve
30 Distal section of sleeve
31 Middle section of sleeve
32 Proximal section of sleeve
33 Clamping ring
34 Fastening sleeve
35 Annular groove
36 Carrier
37 Profiling
38 Profile section
39 Sleeve section
40 Guide tab
41 Transverse bar
42 Shoulder
43 Stop area
44 Bendable area
45 Proximal end
46 Distal end
47 Sleeve
48 First section of the outer shaft
49 Second section of the outer shaft
50 Support tube
51 Support tube
52 Outer shaft tube
53 Outer shaft tube
54 Hose
55 End piece
56 End sleeve
57 Transverse slit
58 First section of the electrode
59 Second section of the electrode
60 Third section of the electrode
61 Fixing place
62 Connection element
63 Slits
64 Overlap area
65 Distal end area
111 Electrode
144 Bendable area

What is claimed is:

1. An electrosurgical instrument for use on biological tissue, comprising:
a handle;
an outer shaft that surrounds an electrode and that is held in the handle; and
an actuation mechanism on the handle to move the outer shaft in an axial direction relative to the electrode;
wherein the outer shaft and the electrode are mechanically connected with one another in a distal end area of the outer shaft in such a way that the electrode can be bent by moving the outer shaft relative to the electrode; wherein the electrode and the outer shaft are arranged so that each of them can rotate about respective longitudinal axes thereof relative to the handle, the electrode being guided by a sliding sleeve that connects the outer shaft and the electrode in a non-rotatable and axially movable manner, and at least sections of the sliding sleeve having a profiling on an inner periphery thereof that positively interlocks with the electrode at at least sections of which are correspondingly profiled, to transfer a torque, and the sliding sleeve and a carriage being rotationally movable and solidly connected in an axial direction of the sliding sleeve to transfer a compressive force, the carriage having a retaining ring that surrounds the sliding sleeve around at least part of an outer periphery thereof.

2. The instrument described in claim 1, wherein the outer shaft has a bendable area in the distal end area, and the electrode is flexible in the bendable area such that the bendable area of the outer shaft is bent by moving the outer shaft relative to the electrode.

3. The instrument described in claim 2, wherein the electrode is fixed at a distal end of the bendable area.

4. The instrument described claim 2, wherein the bendable area has a flexible sleeve that surrounds the electrode.

5. The instrument described in claim 4, wherein a proximal end of the sleeve is connected with a first rigid shaft section, and a distal end of the sleeve is connected with a second rigid shaft section.

6. The instrument described in claim 2, wherein the bendable area has a hose that forms an outer wall of the outer shaft in and/or near the bendable area.

7. The instrument described in claim 1, wherein the electrode includes an inner shaft which has a bendable area in the distal end area, and the inner shaft is flexible in the bendable area such that the bendable area of the inner shaft is bent by moving the outer shaft relative to the inner shaft.

8. The instrument described in claim 7, wherein the inner shaft is mechanically connected, in the distal end area, with the outer shaft by a connection element.

9. The instrument described in claim 7, wherein the bendable area of the inner shaft is formed by opposite slits, each of which extends beyond an axial middle of the inner shaft, forming an overlapping area.

10. The instrument described in claim 9, wherein the slits are separated from one another by approximately 0.2 mm, and an overlap of the slits with respect to the axial middle is approximately 0.6 mm.

11. The instrument described in claim 9, wherein a width of the slits is between 0.1 and 1.0 mm.

12. The instrument described in claim 1, wherein the handle has a braking device that continually exerts a braking force on the outer shaft, and the actuation mechanism forms a rotating wheel with a step-up gear that is connected with the outer shaft to transfer an axial force.

13. The instrument described in claim 12, wherein the rotating wheel comprises a drive gear and at least one driven gear that is non-rotatably connected with the drive gear and that is connected with the outer shaft to transfer the compressive force, a diameter of the driven gear being smaller than that of the drive gear, and wherein the carriage is axially movable in a thrust direction and is connected on one side with the outer shaft and on another side with the step-up gear, the carriage having at least a first gear rack that is arranged parallel to the thrust direction and that meshes with the driven gear.

* * * * *